United States Patent
Das et al.

(10) Patent No.: US 9,713,582 B2
(45) Date of Patent: Jul. 25, 2017

(54) MULTI-LAYERED COSMETIC COMPOSITION

(71) Applicant: The Procter & Gamble Company, Cincinnati, OH (US)

(72) Inventors: Surajit Das, Singapore (SG); Jayant Eknath Khanolkar, Singapore (SG)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 14/684,556

(22) Filed: Apr. 13, 2015

(65) Prior Publication Data

US 2016/0296430 A1    Oct. 13, 2016

(51) Int. Cl.
| | |
|---|---|
| *A61K 8/03* | (2006.01) |
| *A61Q 19/00* | (2006.01) |
| *A61K 8/06* | (2006.01) |
| *A61K 8/73* | (2006.01) |
| *A61K 8/92* | (2006.01) |
| *A61K 8/81* | (2006.01) |
| *A61K 8/86* | (2006.01) |
| *A61K 8/89* | (2006.01) |
| *A61Q 19/10* | (2006.01) |

(52) U.S. Cl.
CPC .......... *A61K 8/06* (2013.01); *A61K 8/03* (2013.01); *A61K 8/73* (2013.01); *A61K 8/735* (2013.01); *A61K 8/8176* (2013.01); *A61K 8/86* (2013.01); *A61K 8/89* (2013.01); *A61K 8/922* (2013.01); *A61Q 19/00* (2013.01); *A61Q 19/007* (2013.01); *A61Q 19/10* (2013.01); *A61K 2800/594* (2013.01)

(58) Field of Classification Search
None
See application file for complete search history.

(56) References Cited

U.S. PATENT DOCUMENTS

| 5,213,799 | A | 5/1993 | Goring |
| 6,138,766 | A * | 10/2000 | Finnerty ............... A62C 5/008 169/14 |
| 6,180,587 | B1 | 1/2001 | Fuller |
| 6,429,177 | B1 | 8/2002 | Williams |
| 6,619,295 | B1 | 9/2003 | Okabe |
| 6,649,174 | B2 | 11/2003 | Najdek |
| 6,649,178 | B2 | 11/2003 | Mohammadi |
| 7,988,981 | B2 | 8/2011 | Di Puccio Pagano |
| 2002/0055562 | A1 | 5/2002 | Butuc |
| 2005/0118214 | A1* | 6/2005 | Najdek ............... A61K 8/03 424/401 |
| 2006/0079418 | A1 | 4/2006 | Wagner |
| 2009/0311200 | A1* | 12/2009 | Lambert ............... A61K 8/03 424/52 |
| 2012/0134939 | A1 | 5/2012 | Ueda |
| 2013/0303634 | A1 | 11/2013 | Matsuzawa |

FOREIGN PATENT DOCUMENTS

| DE | 198 57 425 A 1 | 6/2000 |
| DE | 102012219641 | 4/2014 |
| EP | 258558 | 4/1991 |
| EP | 1475077 | 11/2004 |
| EP | 1572857 | 9/2005 |
| FR | 2663847 | 3/1993 |
| JP | 60078907 | 5/1985 |
| JP | 11335237 | 12/1999 |
| JP | 2001058923 | 3/2001 |
| JP | 2001097841 | 4/2001 |
| JP | 2001213724 | 8/2001 |
| JP | 2002003339 | 1/2002 |
| JP | 2002066297 | 3/2002 |
| JP | 2002294084 | 10/2002 |
| JP | 2004196713 | 7/2004 |
| JP | 2004203764 | 7/2004 |
| JP | 2006-306841 A | 11/2006 |
| JP | 2013075867 | 4/2013 |
| JP | 2014091715 | 5/2014 |
| JP | 2014208634 | 11/2014 |
| KR | 20100121995 | 11/2010 |
| KR | 20110036801 | 4/2011 |
| WO | WO9641613 | 12/1996 |
| WO | WO2010140329 A1 | 12/2010 |
| WO | WO2014018543 | 1/2014 |

OTHER PUBLICATIONS

International Search Report and Written Opinion of the International Searching Authority PCT/US2016/027013; Date of Mailing Jun. 14, 2016; 9 pages.

* cited by examiner

*Primary Examiner* — Abigail Fisher
(74) *Attorney, Agent, or Firm* — S. Robert Chuey

(57) ABSTRACT

A multi-layered cosmetic composition suitable for topical application is provided. The composition comprises an oil layer comprising at least about 5%, by weight of the composition, of natural oil; and an aqueous layer, comprising at least about 0.01%, by weight of the composition, of a polymer selected from the group consisting of a polysaccharide, sodium hyaluronate, or a combination thereof. The multi-layered cosmetic composition is free of surfactant.

10 Claims, 1 Drawing Sheet

MULTI-LAYERED COSMETIC COMPOSITION

TECHNICAL FIELD

The invention relates to a multi-layered cosmetic composition that provides skin conditioning benefits while additionally providing an enhanced aesthetic and sensorial in-use experience.

BACKGROUND

Multi-layer compositions for cosmetic use are well known in the prior art, particularly in the area of cleansers and make-up removers. A multi-layer composition formed with separate oil, alcohol and water layers will often comprise compounds that are incompatible with each other. The different layers are typically separate when at rest, and form an emulsion when agitated. This way the incompatible compounds are kept separate until the time of use of the cosmetic. In addition to enabling the presence of different incompatible compounds, such multi-layer compositions are typically visually appealing and provide an interactive experience for a user.

Most multi-layer products currently on the market are formed with two layers, typically a top oil layer and a bottom aqueous layer that comprises skin care actives, such as humectants, glycols, preservatives, alcohol, salt and water. One or more surfactants are typically provided in either the oil or the aqueous layer to facilitate quick homogenization of the two layers before use. After use and when left to rest, the composition separates back into two distinct layers over a period of hours.

For multi-layer compositions where quicker separation is required, the amount of surfactant may be reduced or eliminated completely. Where no surfactant is provided, the layers will separate immediately after a user stops agitating the composition. This is generally acceptable for cosmetic cleansers, however, for other skin care products (such as moisturizers), it is important to retain the correct ratio of oil to aqueous phase in the homogenized product during application to ensure consistent efficacy and sensory benefits throughout the product usage.

Most multi-layer compositions currently on the market have an oil layer formed mainly, if not entirely, of synthetic oils. Synthetic oils tend to have a purer chemical form than natural oils which make them more predictable and easier to incorporate in different forms of product, such as multi-layer compositions. Replacement of synthetic oils with natural oil(s) in existing multi-layer compositions can significantly compromise the aesthetic benefit currently associated with such products. In this respect, natural oils tend to contain carry over ingredients, such as saponin, that are known to take on a soap-like form when shaken with water. This soap-like form becomes more noticeable, and remains present longer in the presence of a surfactant due to the cumulative foaming effect of the surfactant together with the carry over ingredient. This can lead to the formation of a milky layer at the meeting point between the oil layer and the aqueous layer that may take some time to dissipate.

Surfactants are known to have additional disadvantages of use, such as causing skin irritation by disturbing the skin structure. Furthermore, they may attract oil ingredients into the aqueous phase during storage and transport and vice versa. Thus there is a need to form multi-layer compositions that do not suffer from some of these issues associated with use of a surfactant.

U.S. Pat. No. 7,988,981 discloses a multi-layer composition including an oil layer formed of a mixture of mineral, vegetable and synthetic oils, and an aqueous layer comprising at least one polyol and water soluble salts. U.S. Pat. No. 7,988,981 avoids the negative effects of using a surfactant with natural oils, but this instead leads to a multi-layer composition that, upon agitation, forms a homogenous mixture that separates out again immediately when it is left to rest.

Thus, there is still a need to improve existing multi-layer compositions to provide greater flexibility of choice of ingredients and better control of separation time.

SUMMARY

A multi-layered cosmetic composition suitable for topical application, comprising:
  i) an oil layer, comprising at least 5% of a natural oil; and
  ii) an aqueous layer, comprising between 0.01% to 0.25% of a polymer selected from the group consisting of polysaccharides and sodium hyaluronate,
wherein the multi-layered cosmetic composition is free of surfactant.

The present invention provides a multi-layer composition using natural oils that is capable of emulsification on agitation, but that readily separates in a controlled manner within a period of time that enables a user to repeatedly use the product during a single application without the product separating, and without formation of a milky layer between the oil and aqueous layers.

A method of applying a multi-layered cosmetic composition, comprising:
  a) shaking a multi-layered composition to form an emulsion, said multi-layered composition having:
    i) an oil layer comprising at least 5% by weight of the total composition of natural oil; and
    ii) an aqueous layer comprising at least 0.01% by weight of the total composition of a polymer selected from: a polysaccharide, sodium hyaluronate, or a combination thereof;
  wherein the multi-layered cosmetic composition is free of surfactant;
  b) applying said emulsified composition to a facial skin surface in need of treatment.

BRIEF DESCRIPTION OF THE DRAWINGS

While the specification concludes with claims, it is believed that the same will be better understood from the following description taken in conjunction with the accompanying drawings in which:

DETAILED DESCRIPTION

Figure 1A:
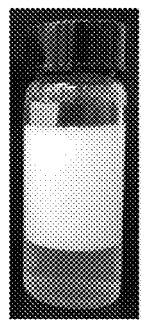
FIG. 1A shows a photo of a multi-layer cosmetic composition of the prior art (i.e., including a surfactant) at 2 hours post agitation.

All percentages are weight percentages based on the weight of the total composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Cosmetic composition" as used herein, means compositions suitable for topical application on mammalian keratinous tissue.

"Free of" means that the composition comprises less than a trace amount, for example, less than 0.001% by weight of the composition, of an ingredient and more particularly that the ingredient has not been intentionally added, but may be included as a by-product or carry-over of another ingredient.

"Safe and effective amount" means an amount sufficient to induce one or more biological effects, but low enough to avoid serious side effects, (e.g., undue toxicity or allergic reaction).

"Humectant" as used herein, means a substance which provides the skin with water-retention benefits.

"Keratinous tissue" as used herein refers to keratin-containing layers disposed as the outermost protective covering of mammals which includes, but is not limited to, skin, hair, nails, cuticles, etc.

"Salts" as used herein, includes but is not limited to sodium, potassium, calcium, ammonium, manganese, copper, and/or magnesium salts of a given compound.

"Silicone oil" as used herein refers to those oils containing at least one silicon atom, and especially containing Si—O groups.

"Skin care actives" as used herein, means compounds that, when applied to the skin, provide a benefit or improvement to the skin. It is to be understood that skin care actives are useful not only for application to skin, but also to hair, nails and other mammalian keratinous tissue.

Multi-Layer Composition

Described hereafter are various embodiments of multi-layer cosmetic compositions formulated for topical application to mammalian keratinous tissue, in particular to human skin. The multi-layer cosmetic composition of the present invention is preferably intended for use as a moisturizer and falls within the category of a skin care oil. The multi-layer composition comprises at least two separate layers in direct contact with one another where: (1) a bottom aqueous layer comprising a polymer selected from the group consisting of polysaccharides and sodium hyaluronate, and combinations thereof, and (2) a top oil layer comprising natural oils and possibly further comprising synthetic oils. The multi-layer composition is essentially free of surfactants. When agitated, the aqueous layer and oil layer mix together to form a single, homogenous composition, ready for application by a user. Use of a polymer such as a polysaccharide or sodium hyaluronate in the aqueous phase facilitates homogeneity of the composition for a short period of time after it is left to rest, preferably between about 2, 4, 6 or 8 minutes and 30, 40, 50 or 60 minutes, without the need for a surfactant. Such polymers typically provide additional sensorial benefits such as a smooth feel, long lasting moisturisation and occlusive coatings on skin. Furthermore, use of such a polymer instead of a surfactant further prevents formation of a foamy layer between the aqueous and oil layers following separation and reduces the chance of irritation being caused by a surfactant.

Oil Layer

The multi-layer composition described herein may contain one or more oils in the oil layer. These oils may be natural (e g, mineral and/or vegetable) and synthetic, or a combination thereof. Liposoluble or lipodispersible additives may also be present in the oil layer. Examples of natural oils that may be included in the composition include, but may be selected from the group consisting of jojoba oil, avocado oil, olive oil, rice bran oil, argan oil, grapeseed oil, sunflower oil, safflower oil, sesame seed oil, apricot kernel oil, macadamia seed oil, rice germ oil, chamomile oil, almond oil, rosehip seed oil, and combinations thereof.

Natural oils have several skin benefits, such as moisturisation, anti-oxidant, anti-inflammatory, skin conditioning, skin elasticity, anti-bacterial, anti-fungal, anti-aging, skin softening, skin nourishment. For example, jojoba oil has moisturisation and anti-fungal benefits; avocado oil has anti-oxidant, anti-aging, anti-inflammatory benefits and contains omega-3 fatty acids; olive oil acts as an anti-oxidant, skin conditioning agent, moisturizer, and restores skin elasticity; rice bran oil is an anti-oxidant, moisturizer, emollient and contains γ-oryzanol, plant sterol, vitamin E; and argan oil is a moisturizer, acting against juvenile acne and flaking of skin.

Natural oils such as those listed above tend to contain carry-over ingredients, for example, saponin, an amphipathic glycoside that produces a soap-like foam when shaken in an aqueous solution. Other such carry-over ingredients include, but are not limited to stearic acid, linoleic acid, and triglycerides, etc.

In embodiments, the multi-layer composition comprises from 20%, 30%, 35% and 40% to 50%, 60%, 70% and 80% by weight of the composition of an oil layer. Preferably, the composition comprises at least 5%, 10%, 20% or 30% by weight of the composition of natural oil. In a preferred embodiment, the oil layer contains 100% of natural oil that is a blend of, for example, rice bran oil, jojoba oil and olive oil.

Suitable synthetic oils are selected from the group consisting of squalane, isopropyl isostearate, isohexadecane, isopropyl myristate, and combinations thereof.

The silicone oil may be chosen from non-volatile silicone oils and volatile silicone oils, and mixtures thereof.

Aqueous Layer

The aqueous layer of the composition constitutes the bottom layer/phase of the two requisite layers of the multi-layer composition. The aqueous layer comprises water and, if desired, one or more of any water-soluble or water-dispersible additive. The water used may be any water, including tap, sterile demineralised water and/or a floral water such as rosewater, cornflower water, chamomile water or lime water, and/or a natural mineral water or spring water. In an embodiment, deionized water is preferably used. Water from natural sources including mineral cations may also be used, depending on the desired characteristic of the product. In one preferred embodiment, water may be mixed fermented biological cultures or its filtrates. A highly preferred commercial source of this kind of fermented biological culture is Galactomyces ferment filtrate by the tradename SK-II Pitera®.

In embodiments, the multi-layer composition comprises from about 20%, 30% or 40% to about 50%, 60%, 70% or 80%, of the aqueous layer.

The aqueous layer comprises from about 0.01%, 0.025%, 0.05%, 0.075% to about 0.1%, 0.15%, 0.2% or 0.25%, by weight of the composition of one or more water-soluble polymers, including at least one selected from the group consisting of polysaccharides and sodium hyaluronate, and combinations thereof.

Examples of a polysaccharide include natural or synthetic varieties of starches, gums and cellulosic ethers. One example of a suitable starch is pullulan. Suitable gums include xanthan, pectin, karaya, Arabic, gelatin, agar, guar, carrageenan, alginate, and combinations thereof. Suitable cellulosic ethers include hydroxyethyl cellulose, hydroxypropyl cellulose, hydroxypropyl methylcellulose, methylcellulose and sodium carboxy methylcellulose, and combinations.

Preferably, the polysaccharide used in the aqueous layer of the multi-layer composition is xanthan gum. Preferably, the multi-layer composition of the present invention comprises from about 0.01%, 0.025%, 0.05%, 0.075% to 0.1%, 0.15%, 0.2% or 0.25%, by weight of the composition, of a polysaccharide, preferably xanthan gum.

Additionally and/or alternatively to inclusion of a polysaccharide, the aqueous layer may comprise sodium hyaluronate, a sodium salt of hyaluronic acid. Preferably, the multi-layer composition of the present invention comprises from about 0.01%, 0.025%, 0.05%, 0.075% to 0.1%, 0.15%, 0.2% or 0.25%, by weight of the composition, of sodium hyaluronate.

Polymers, such as the polysaccharides and sodium hyaluronate described herein, provide benefits with respect to short term emulsion, moisturisation and sensory feel. Specifically, polymers such as xanthan gum and sodium hyaluronate increase the viscosity of the aqueous phase which helps to control the amount of time droplets (oil or water) coalesce. Furthermore, sodium hyaluronate provides a smooth feeling on the skin—providing sensorial benefits when the product is used by a consumer. Sodium hyaluronate and xanthan gum are both also known to provide a coating on skin which prevents skin moisture evaporation while maintaining good long lasting skin moisturisation. Sodium hyaluronate also acts as a humectant, binding with water molecules leading to long lasting moisturisation of skin.

In certain embodiments, the aqueous layer comprises a combination of a polysaccharide and sodium hyaluronate to provide desirable sensory and moisturisation benefits, at the same time as facilitating the required homogenization. In this respect, excessive amounts of either one of a polysaccharide or sodium hyaluronate may have a negative sensorial impact. For example, too much sodium hyaluronate may provide a slimy sensation on skin, while xanthan gum sometimes exhibits a tacky sensation. When combined, it is possible to balance the amount of polymer needed to provide the required homogenization while avoiding some of these negative sensations.

The use of polysaccharides and/or sodium hyaluronate to facilitate emulsion provides more flexibility in choice and ratio of oils to aqueous ingredients. It is understood that the choice of surfactant is normally tied to specific oil types and ratios of oil to water phase. Typically, different oil and/or aqueous combinations may need different surfactants with different HLB values in order to provide a stable emulsion. By contrast, it is believed that the current polymer combinations can be used for a variety of oils and different oil to water phase ratios. Polymers cause homogenization/emulsification via a different mechanism to surfactants. Surfactants break surface tension, whereas polymers delay phase separation by increasing the viscosity of one of the component parts. Accordingly, it is believed that using polymers as the emulsifier in multi-layer compositions provides a unique and flexible platform technology, where the same emulsification system may be used with different oil types (synthetic or natural) or different ratios of oil to aqueous phase.

The aqueous layer of the multi-layer composition may further comprise other polymers, for example, but not limited to, polyvinylpyrrolidone (PVP), polyethylene oxide and other polyvinyl polymers that provide sensorial and textural benefits to the composition. If used at a sufficiently high level (for example, at least 10% by weight of the total composition), PVP alone can be used to provide the desired homogenization. However, preferably, the composition contains a combination of a polysaccharide such as xanthan gum, sodium hyaluronate and PVP. For example, a well balanced composition may contain between 0.01% to 0.05%, preferably 0.03% of sodium hyaluronate, between 0.01 and 0.02%, preferably 0.01% of xanthan gum and between 0.01% and 1%, preferably 0.1% of PVP.

Other Ingredients

The composition may include one or more other ingredients, which will be incorporated in either the oil or water layer depending on their hydrophilic or lipophilic nature, for instance fragrances, preservatives and bactericides, dyes, softeners, buffers, humectants, UV-screening agents (or sunscreens), or a pH regulator (for example citric acid or sodium hydroxide), agents which facilitate phase separation, polymers, and mixtures thereof. These ingredients may provide benefits to a user's skin and/or enhance the visual appearance or sensory experience for a consumer.

For example, the composition may include a natural colourant that is oil or water soluble (and can thus be included in the oil or water layer). For example, the natural colourant may be beta-carotene, turmeric/curcumin, riboflavin, chlorophyll, beetroot red, etc.

Preservatives that may be used include parabens, benzyl alcohol, di-sodium EDTA, phenoxyethanol, sodium benzoate, hexanediol and caprylyl glycol. The preservative may be included in the oil or aqueous phase to prevent microbial growth in the product.

The aqueous phase of the composition may include humectants, including but not limited to glycerin, sodium pyrolidone carbonic acid or glycols to enhance acute and chronic skin moisturisation benefits (for example).

The composition may further include an anti-oxidant, for example including, but not limited to, tochopheryl acetate, butylated hydroxytoluene, butylated hydroxyanisole, tochopherol. As an example, tochopheryl acetate may be included in the oil phase to prevent the natural oils from oxidizing or becoming rancid.

Active(s) that may be present in the composition depend on the final purpose of the composition. Actives that may be present in a skin care composition include, for example, enzymes (for example lactoperoxidase, lipase, protease, phospholipase and cellulases); flavonoids, such as isoflavones; moisturizers such as protein hydrolysates; hyaluronic acid; anti-inflammatory agents; procyannidol oligomers; vitamins, for instance vitamin A (retinol), vitamin E (tocopherol), vitamin C (ascorbic acid), vitamin B5 (panthenol), vitamin B3 (niacinamide), derivatives of these vitamins (especially esters) and mixtures thereof; urea; caffeine; depigmenting agents such as kojic acid, hydroquinone and caffeic acid, salicylic acid and its derivatives; α-hydroxy acids such as lactic acid and glycolic acid and derivatives thereof; retinoids such as carotenoids and vitamin A derivatives; hydrocortisone; melatonin; algae extracts; fungal extracts; plant extracts, yeast extracts or bacterial extracts; steroids; anti-bacterial active agents for instance 2,4,4'-trichloro-2'-hydroxydiphenyl ether (or triclosan), 3,4,4'-trichlorocarbanilide (or triclocarban) and the acids indicated above, and especially salicylic acid derivatives, tensioning agents; ceramides; essential oils; and mixtures thereof; and any active agent suitable for the final purpose of the composition, including UV actives, such as octocrylene, homosalate.

Method of Use

Various cosmetic treatments may be employed. Skin surfaces of the most concern tend to be those not typically covered by clothing such as facial skin surfaces, hand and arm skin surfaces, foot and leg skin surfaces, and neck and chest skin surfaces. In particular, facial skin surfaces, including the forehead, perioral, chin, periorbital, nose, and/or cheek skin surfaces, may be treated with the cosmetic compositions described herein.

The treatment method may include applying the cosmetic composition to a previously identified area of skin in need of treatment (e.g., where fine lines, wrinkles or age spots can be seen and/or to improve skin tone evenness). Many regimens exist for the application of the cosmetic composition. As an example, the cosmetic composition may be applied at least once a day, twice a day, or on a more frequent daily basis, during a treatment period. Typically, the cosmetic composition may be applied in the morning and/or in the evening before bed.

The treatment period is ideally of sufficient time to provide an improvement in the appearance of the age spots or skin tone evenness. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the cosmetic composition is applied at least once a day during a treatment period of at least 4 weeks, 8 weeks, or 12 weeks. In one embodiment the cosmetic composition is applied twice a day during a treatment period of at least 4 weeks, 8 weeks, or 12 weeks.

The multi-layer composition described above may be packaged in a single-compartment container, e.g., a jar or bottle. In an alternative embodiment, the two phases of the composition may be stored in independent compartments of the same bottle, with a further cavity or system to facilitate mixing them together prior to use. Such packages are described, for example, in EP-A-497256 and FR-A-2697233. Before use, i.e., when in a rest state, the composition will be formed in two or more distinct layers. In the embodiment described above, an oil layer sits directly above an aqueous layer. The user is required to vigorously shake the container (for about 5 to 20 seconds) before use, to agitate the composition, causing the two layers to homogenize. Where the ratio of oil phase to aqueous phase is quite high, the oil coats the aqueous droplets to form a water-in-oil emulsion. Conversely, where there is a higher ratio of aqueous phase to oil phase, the aqueous phase coats the oil droplets leading to an oil-in-water emulsion. The amount of xanthan gum and/or sodium hyaluronate in the composition determines the viscosity of the aqueous phase which controls the amount of time the droplets (oil or water) stay commingled. The emulsion should remain stable for at least 2 minutes so that a consumer using the product has time to apply the emulsified product to their skin. If the product starts separating before the consumer has finished applying the product, then the ratios of product they are applying to their skin will vary for each use.

Preferably, the maximum time to separation will be 30 minutes, so that separation of the product is visible within a timeframe that a consumer may still be in the presence of the product.

The multi-layer composition may take the form of a moisturizer, toner, essence, serum, cream or any other known moisturizing or hydrating skin care composition.

Method of Making a Multi-Layer Composition

The following method is an example of one method of making a multi-layer composition of the invention and should not be construed as limiting the invention. Other known methods of forming a multi-layer composition may be used.

a. Oil Layer—Oils of the composition are weighed in a container and mixed using a suitable mixing device, such as a magnetic stirrer or anchor mixer, at 100-200 rpm at room temperature for 10-25 minutes. Other lipophilic ingredients are weighed and mixed with the oil using a suitable mixing device at 100-200 rpm at 25-60° C. until the mixture becomes clear. Perfume is added to the oil mixture and mixed at 100-200 rpm at room temperature for 10-25 minutes.

b. Aqueous Layer—The preservatives are mixed together in a container at 100-200 rpm for 10-20 minutes. Xanthan gum is dispersed in glycerin, while sodium hyaluronate is added to hot water (60-80° C.) and dissolved using a suitable high speed mixing device such as a disperser until arriving at a clear solution. The xanthan gum-glycerin dispersion is added to the hot sodium hyaluronate solution and mixed together for 5 to 15 minutes. After cooling down to room temperature, sodium benzoate and disodium EDTA are mixed together with the Galactomyces ferment filtrate until all materials are dissolved and the solution becomes clear. All other ingredients are added to the aqueous solution and mixed until a clear solution is formed.

c. Multi-layer composition—the aqueous phase, oil phase and any other phases are added together at the desired ratio and allowed to rest until they have separated into their respective layers.

EXAMPLES

The following examples are given solely for the purpose of illustration and are not to be construed as limiting the invention, as many variations thereof are possible. All measurements below are % by weight of the total composition.

| | Sample 1 (% wt) | Sample 2 (% wt) |
|---|---|---|
| Oil phase | | |
| Rice bran oil | 20.000 | 20.000 |
| Jojoba oil | 20.000 | 20.000 |
| Olive oil | 10.000 | 10.000 |
| Aqueous phase | | |
| De-ionized water | 40.597 | 40.060 |
| Butylene Glycol | 4.000 | 4.000 |
| Glycerin | 5.000 | 5.000 |
| Sodium Benzoate | 0.300 | 0.300 |
| Methyl paraben | 0.100 | 0.100 |
| Sodium hyaluronate | | 0.020 |
| Xanthan gum | | 0.020 |
| Polyvinylpyrrolidone | | 0.500 |
| PEG-20 sorbitan cocoate | 0.003 | |
| Total | 100.000 | 100.000 |

Figure 1B:
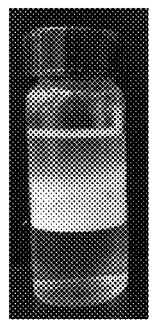
FIG. 1B shows a photo of the composition of FIG. 1A at 12 hours post-agitation.
Figure 1C:
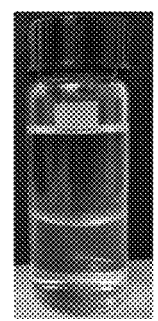
FIG. 1C shows a photo of the multi-layer composition of the present invention at 2 hours post-agitation.

A comparison was made of the separation of the oil and aqueous phase in two comparative samples, a first (sample 1) incorporating 0.003% of surfactant (PEG-20 sorbitan cocoate) in the aqueous phase and a second (sample 2) where the surfactant is replaced with a blend of polymers, namely 0.02% of xanthan gum, 0.02% of sodium hyaluronate and 0.5% of polyvinylpyrrolidone. FIGS. 1A to 1C show the multi-layer compositions post-agitation and after the product has been left to rest for a period of time. FIGS. 1A and 1B show sample 1 at 2 hours and 12 hours post-agitation, whereas FIG. 1C shows sample 2 at 2 hours post-agitation. For completeness, it should be assumed that all samples had the same emulsified look immediately post-agitation. It can be seen in FIG. 1A that 2 hours after agitation of sample 1, the bottom, aqueous layer has separated from the oil layer, however, the oil layer is relatively opaque and has a white, milky colour. FIG. 1B shows that 12 hours after being left to rest, a significant part of the oil phase that borders the aqueous phase is still opaque with a white, milky colour. By contrast, 2 hours after being left to rest, sample 2 has separated into clear and distinct oil and aqueous layers with no presence of any milky layer between the aqueous and oil layers (FIG. 1C).

Thus, it can be seen that inclusion of even a small amount of surfactant in a multi-layer composition comprising natural oil may negatively affect separation of the layers when left to rest.

|  | Example 1 (% wt) | Example 2 (% wt) | Example 3 (% wt) | Example 4 (% wt) |
| --- | --- | --- | --- | --- |
| Oil phase |  |  |  |  |
| Rice bran oil | 20.000 | 20.000 | 20.000 | 20.000 |
| Jojoba oil | 20.000 | 20.000 | 20.000 | 20.000 |
| Olive oil | 10.000 | 10.000 | 10.000 | 10.000 |
| Aqueous phase |  |  |  |  |
| De-ionized water | 49.995 | 49.950 | 49.900 | 49.750 |
| Xanthan gum | 0.005 | 0.050 | 0.100 | 0.250 |
| Total | 100.000 | 100.000 | 100.000 | 100.000 |
| Separation starts at | <1 min | 10 min | 20 min | 60 min |

Each of Examples 1 to 14 was shaken vigorously for a period of 15 seconds to form an emulsion, before being laid to rest. The time lapse between being laid to rest and the first sign of separation is shown for each example. The first sign of separation was visually determined with either of the aqueous or oil layers started to become transparent. Examples 1 to 4 include differing amounts of xanthan gum as the only polymer. From Example 1, it can be seen that inclusion of less than 0.01% of xanthan gum the emulsified composition starts separating before the desired minimum of 2 minutes. This is undesirable for functional and aesthetic reasons. Functionally, it is expected that a user requires approximately 2 minutes to apply a moisturizing product to all relevant body parts. Thus, if the emulsified composition separates before the user has finished applying the product, the product being applied may have an incorrect ratio of ingredients. Examples 2, 3 and 4 show that inclusion of up to 0.25% of xanthan gum increases the separation time within an acceptable range, with a preference for Examples 2 and 3 where the separation time is less than 30 minutes.

|  | Example 5 (% wt) | Example 6 (% wt) | Example 7 (% wt) | Example 8 (% wt) |
| --- | --- | --- | --- | --- |
| Oil phase |  |  |  |  |
| Rice bran oil | 20.000 | 20.000 | 20.000 | 20.000 |
| Jojoba oil | 20.000 | 20.000 | 20.000 | 20.000 |
| Olive oil | 10.000 | 10.000 | 10.000 | 10.000 |
| Aqueous phase |  |  |  |  |
| De-ionized water | 49.995 | 49.950 | 49.900 | 49.750 |
| Sodium hyaluronate | 0.005 | 0.050 | 0.100 | 0.250 |
| Total | 100.000 | 100.000 | 100.000 | 100.000 |
| Separation starts at | <1 min | 5 min | 9 min | 3 min |

Examples 5 to 8 include differing quantities of sodium hyaluronate as the sole polymer. As can be seen in Example 5, where less than 0.01% of sodium hyaluronate is included, the separation time is less than 1 minute. In Examples 6 and 7, the amount of sodium hyaluronate is increased (to a maximum of 0.1%) and the separation time increases (within the acceptable range). Surprisingly, in Example 8, the amount of sodium hyaluronate is increased to 0.25% and the separation time begins to decrease (though it remains within the acceptable range). As can be seen in Example 11, when the amount of sodium hyaluronate is further increased to 0.5%, the separation time further decreases to less than 1 minute (i.e., out of the acceptable range). Thus, it can be seen that there is a maximum acceptable amount of sodium hyaluronate that may be included in a composition where a separation time of greater than 2 minutes is desirable.

|  | Example 9 (% wt) | Example 10 (% wt) | Example 11 (% wt) |
| --- | --- | --- | --- |
| Oil phase |  |  |  |
| Rice bran oil | 20.000 | 20.000 | 20.000 |
| Jojoba oil | 20.000 | 20.000 | 20.000 |
| Olive oil | 10.000 | 10.000 | 10.000 |
| Aqueous phase |  |  |  |
| De-ionized water | 49.930 | 49.900 | 49.495 |
| Xanthan gum | 0.020 | 0.080 | 0.005 |
| Sodium hyaluronate | 0.050 | 0.020 | 0.500 |
| Total | 100.000 | 100.000 | 100.000 |
| Separation starts at | 10 min | 20 min | <2 min |

Examples 9 and 10 above show preferable examples comprising both xanthan gum and sodium hyaluronate, both of which result in an acceptable separation time (10 and 20 minutes respectively).

|  | Example 12 (% wt) | Example 13 (% wt) |
| --- | --- | --- |
| Oil phase |  |  |
| Rice bran oil | 70.000 | 30.000 |
| Aqueous phase |  |  |
| De-ionized water | 29.560 | 69.560 |
| Xanthan gum | 0.020 | 0.020 |
| Sodium hyaluronate | 0.020 | 0.020 |
| Polyvinylpyrrolidone | 0.400 | 0.400 |
| Total | 100.000 | 100.000 |
| Separation starts at | 4 min | 5 min |

Example 12 contains an oil phase to aqueous phase ratio of 70:30, whereas Example 13 contains an oil phase to aqueous phase ratio of 30:70. Phase separation times for both examples are within acceptable range (greater than 2 minutes, preferably less than 60 minutes. This shows the described polymer system supports multiphase compositions at different oil phase to aqueous phase ratios.

|  | Example 14 (% wt) |
|---|---|
| Oil phase |  |
| Squalane | 15.000 |
| Jojoba Oil | 10.000 |
| Avocado Oil | 9.000 |
| Olive Fruit Oil | 8.000 |
| Rice Bran Oil | 8.000 |
| Isohexadecane | 6.000 |
| Tocopherol Acetate | 0.500 |
| Dow Corning 200 Fluid ® 5 Cst | 3.000 |
| Perfume | 0.500 |
| Aqueous phase |  |
| Galactomyces ferment filtrate | 15.000 |
| De-ionized Water | 13.260 |
| Sodium Benzoate | 0.200 |
| Methylparaben | 0.100 |
| Butylene Glycol | 4.000 |
| Glycerin | 5.000 |
| Sodium Hyaluronate | 0.020 |
| Xanthan gum | 0.020 |
| Polyvinylpyrrolidone | 0.400 |
| Sodium pyrolidone carbonic acid | 2.000 |
| Total | 100.000 |
| Separation starts at | 5 min |

Example 14 includes a combination of natural oil, synthetic oil, silicone oil, anti-oxidants and perfume in the oil phase, and a combination of preservatives, humectants, fermented filtrate and polymers in the aqueous phase with an overall ratio of 60:40 of oil phase to aqueous phase. The phase separation time of this example is also within acceptable range. This indicates that inclusion of other commonly used ingredients in the formula is possible while maintaining the desired phase separation profile.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40%" is intended to mean "about 40%."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-layered cosmetic composition suitable for topical application, comprising:
   i) an oil layer comprising at least about 5%, by weight of the composition, of natural oil; and
   ii) an aqueous layer, comprising at least about 0.01%, by weight of the composition, of a polymer selected from the group consisting of sodium hyaluronate, or a combination of sodium hyaluronate with xanthan gum;
   wherein the multi-layered cosmetic composition is free of surfactant;
   said composition containing less than 0.50% of said sodium hyaluronate said composition having a separation time greater than 2 minutes past-agitation.

2. A multi-layered cosmetic composition as claimed in claim 1, wherein the aqueous layer comprises from about 0.05% to about 0.10% of said sodium hyaluronate.

3. A multi-layered cosmetic composition as claimed in claim 2, wherein said aqueous layer comprises from about 0.01% to about 0.25% of a combination of xanthan gum and sodium hyaluronate.

4. A multi-layered cosmetic composition according to claim 1, wherein the aqueous layer further comprises polyvinylpyrrolidone (PVP), polyethylene oxide, or a combination thereof.

5. A multi-layered cosmetic composition according to claim 1, wherein the natural oil comprises carry-over ingredients.

6. A multi-layered cosmetic composition according to claim 1, further comprising a silicone layer.

7. A multi-layered cosmetic composition according to claim 1, wherein the composition is intended for use as a moisturizer, toner, essence, serum or cream.

8. A method of applying a multi-layered cosmetic composition according to claim 1, comprising:
   a) shaking said composition and
   b) applying said shaken emulsified composition of step (a) to a facial skin surface in need of treatment.

9. A multi-layered cosmetic composition suitable for topical application, comprising:
   i) an oil layer comprising about 50% by weight of the composition of natural oil; and
   ii) an aqueous layer, comprising:
      a) from about 0.01% to about 0.05% by weight of the composition of sodium hyaluronate; and
      b) from about 0.01% to about 0.02% by weight of the composition of xanthan gum;
   wherein the multi-layered cosmetic composition is free of surfactant;
   said composition having a separation time greater than 2 minutes past-agitation.

10. A multi-layered composition as claimed in claim 9, further comprising from about 0.01% to about 1% by weight of the composition of polyvinylpyrrolidone (PVP).

* * * * *